United States Patent [19]

Lingappa et al.

[11] 4,349,355
[45] Sep. 14, 1982

[54] METHANE GENERATOR

[76] Inventors: Banadakoppa T. Lingappa; Yamuna Lingappa, both of 4 McGill St., Worcester, Mass. 01607

[21] Appl. No.: 287,767

[22] Filed: Jul. 29, 1981

[51] Int. Cl.³ ............................................. C02F 11/04
[52] U.S. Cl. ..................... 48/111; 210/180; 210/DIG. 9; 422/184; 435/289; 435/316; 435/801
[58] Field of Search ................. 48/111; 210/179, 180, 210/DIG. 9; 435/289, 316, 801; 422/184

[56] References Cited

U.S. PATENT DOCUMENTS

| | | | |
|---|---|---|---|
| 663,623 | 12/1900 | Cameron et al. | |
| 2,202,772 | 5/1940 | Durdin | 210/DIG. 9 |
| 3,288,295 | 11/1966 | Kelly | 210/DIG. 9 |
| 4,100,023 | 7/1978 | McDonald | 195/27 |
| 4,157,958 | 6/1979 | Chow | 210/12 |
| 4,256,837 | 3/1981 | Fluri et al. | 210/DIG. 9 |

OTHER PUBLICATIONS

Lingappa, B. T. and Yamuna, "Family-Size Methane Generators", Solar Age, pp. 16–18, Mar. 1979.
"A Family-Sized Methane Generator", Acres U.S.A., vol. 10, p. 21, Feb. 1980.

*Primary Examiner*—Peter F. Kratz
*Attorney, Agent, or Firm*—Blodgett & Blodgett

[57] ABSTRACT

Apparatus for generating methane from degradable organic material, the apparatus consisting of a tank containing the material in a liquid slurry and gas collector slidably mounted in its upper portion, the gas collector having rods which extend downwardly through a slotted retainer into the organic material for agitating the organic material within the liquid slurry.

10 Claims, 4 Drawing Figures

METHANE GENERATOR

BACKGROUND OF THE INVENTION

As early as 1776, Alessandro Volta recorded his observation that a combustible gas is generated from decaying vegetable matter in the sediments of lakes and ponds. By 1906 this process was known to be a complex microbial fermentation that generated methane by the bioconversion of cellulose and carbon dioxide. For years the development of methane generators, making use of sewage sludge, took place, usually on a large scale by municipalities. There are, for instance, many sewerage disposal plants which make use of sewage sludge for generating a gas which is subsequently burned to provide energy for use in carrying on the sewage processes. Many of these methane generators that use sewage sludge are able to sell the excess gas for a profit. This led to the development of methane generators for converting animal manure to produce methane, commonly referred to as "biogas".

It has been contemplated that there are certain desirable aspects in making use of the methane generating process in rural homes and, particularly on farms. Small domestic methane generators have been installed since 1946 in India where the Gandhian philosophy of coexisting with nature has been particularly strong. This philosophy stresses simplicity, self-sufficiency, and harmony with nature. Most of these small domestic generators have made use of animal manure and, therefore, have been restricted to farms. However, there is no reason why the concept cannot be applied to domestic installation in any location, particularly if unmilled agricultural and domestic waste are used as the basic feed stock. Nevertheless, one of the major problems encountered in attempting to popularize such small domestic methane generators has been the fact that the coarse solids in the sludge have a tendency to rise to the top, cake up and fail to decompose. Such a mat of solids tends to accumulate on the upper region of the body of liquid slurry, so that gas production is drastically reduced. In order to eliminate such stratification, expensive particle reduction by milling the solids and keeping the particles in suspension by costly process of continuous agitation and mixing are necessary. These and other difficulties experienced with the prior art devices have been obviated in a novel manner by the present invention.

It is, therefore, an outstanding object of the invention to provide a methane generator in which gas is generated from unpulverized organic material and is allowed to flow freely from a body of liquid sludge into a hollow collector.

Another object of this invention is the provision of a methane generator in which organic waste solids are maintained submerged in the body of waste slurry.

A further object of the present invention is the provision of a methane generator, particularly adapted for domestic or farm use operating with a slurry of domestic waste, animal manure and many other types of unpulverized organic matter.

It is another object of the instant invention to provide a methane generator which is simple in construction, which is inexpensive to manufacture, and which is capable of a long life of useful service with a minimum of maintenance.

A still further object of the invention is the provision of a methane generator for domestic or farm use whose cost can be amortized over a fairly short period of time and which is operated with a minimum of care i.e., has a passive operation.

It is a further object of the invention to provide a methane generator which is capable of directly converting coarse organic material such as paper, leaf makings, grass clippings, lumps of garbage, chopped hay or pieces of crop residue without first milling the organic material and making it into slurry.

SUMMARY OF THE INVENTION

In general, the invention consists of a methane generator consisting of tank with an open top in which a gas collector is vertically and rotatably slidable. A feed means is provided for introducing raw slurry and organic solids through the gas collector deep into the tank and conduit means is provided for removing methane from the gas collector. A retainer is located in the upper portion of the tank, the retainer having apertures. Rods extend downwardly from the collector and pass through the apertures in the retainer into a body of solids in the slurry located in the tank. The gas collector goes up when filling with methane gas and comes down when the gas is extracted. This downward motion causes the rods to pierce through the solids that are held under the retainer.

More specifically, the collector is free to rotate to and fro in the tank and the apertures in the retainer are concentric slots which enable the rods to move laterally as well as vertically. A heat exchanger is located outside the lower portion of the tank to maintain the slurry at a predetermined temperature for microbial action. An overflow pipe is located on the tank at a substantial distance above the retainer.

BRIEF DESCRIPTION OF THE DRAWINGS

The character of the invention, however, may be best understood by reference to one of its structural forms, as illustrated by the accompanying drawings, in which.

DESCRIPTION OF THE PREFERRED EMBODIMENT

Figures 1, 2:
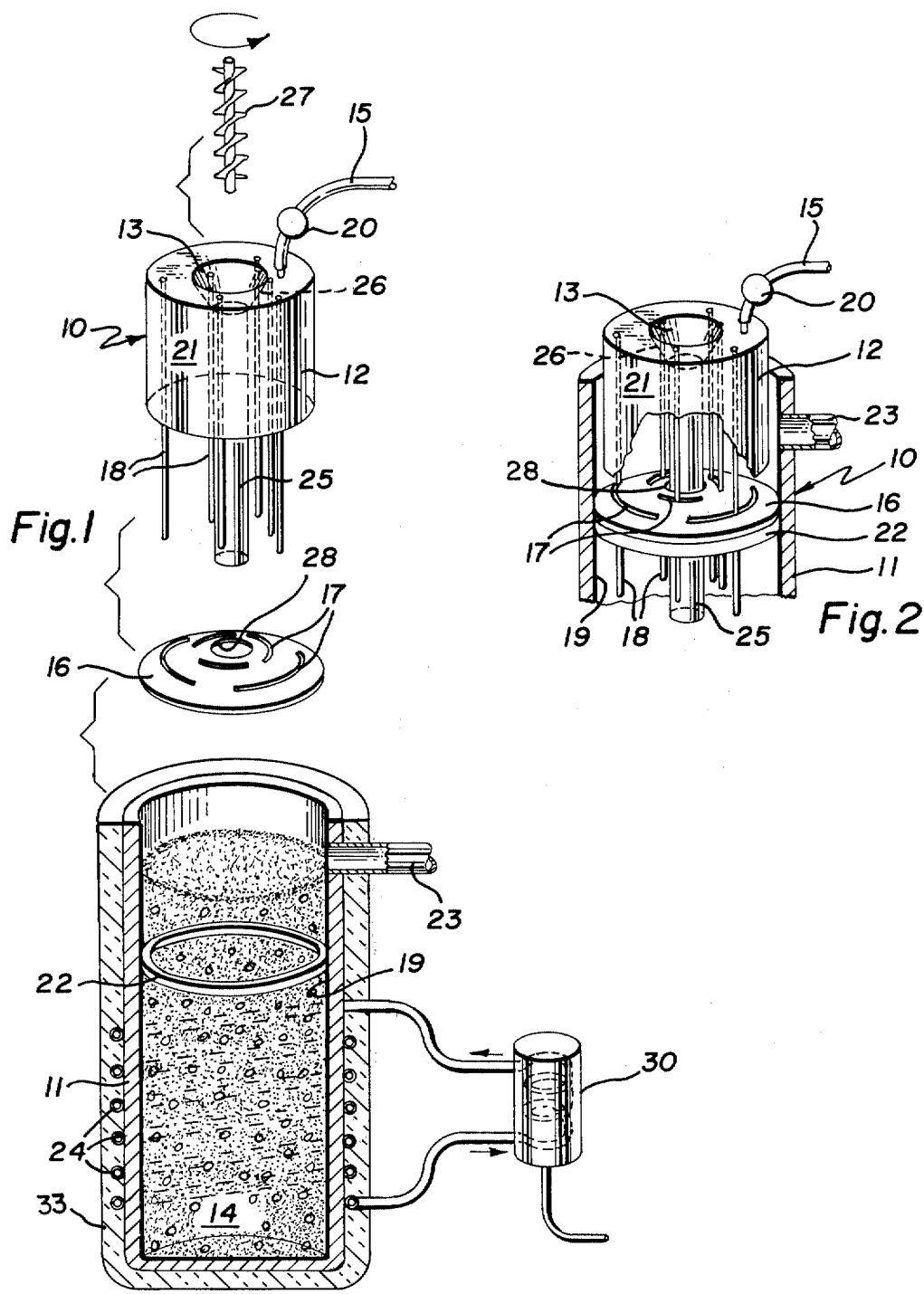
FIG. 1 is an exploded perspective view of a methane generator incorporating the principles of the present invention.
FIG. 2 is an enlarged sectional view of the upper portion of the generator.
Figure 4:
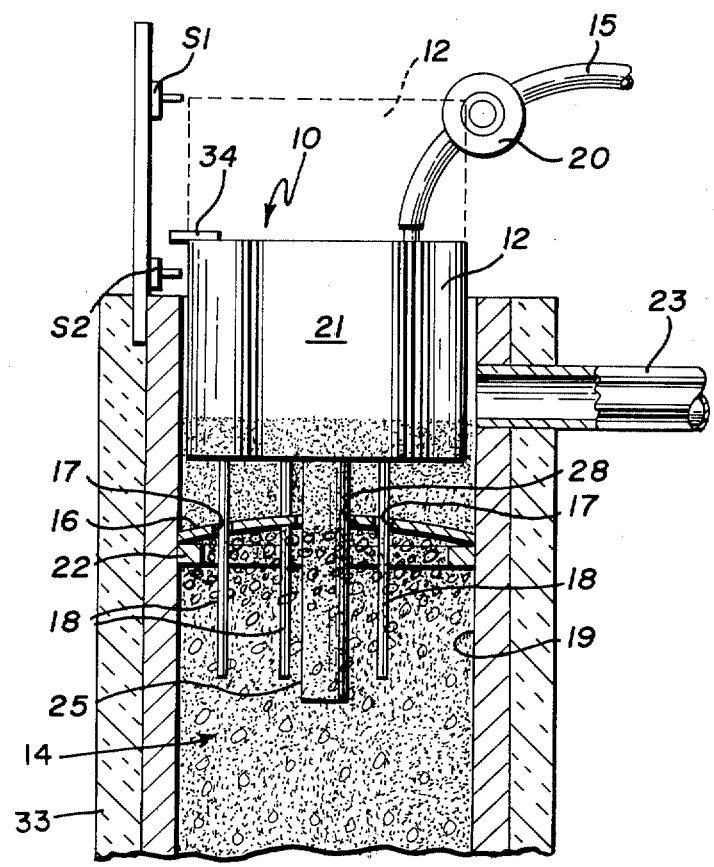
FIG. 4 is a fragmentary sectional view of the generator.

Referring first to FIGS. 1 and 2, wherein are best shown the general features of the invention, the methane generator, indicated generally by the reference numeral 10, is shown as including an open-topped tank 11 enclosed with an insulating jacket 33. The tank is of fairly heavy construction and may be made of cement, metal or fiberglass-reinforced plastic. A gas collector 12 is vertically and rotatably slidable in the tank and is preferably made of relatively light-weight and leak-proof construction, so that it can float and move upwardly under gas pressure. A feed means 13 is provided centrally of the collector for introducing raw slurry through the collector deep into the tank. A conduit means 15 extends from the upper portion of the collector for removing methane from the gas collector, there being a double acting solenoid valve 20 to regulate the low of product gas. Solenoid valve 20 has two cores. Energization of a first core shifts the valve to the closed position and energization of a second core shifts the valve to the open position. Referring also to FIG. 4, valve 20 is controlled by an upper level switch S1 and a lower level switch S2. When upper level switch S1 is closed the second core is energized and the valve is shifted to the open position. When lower level switch S2 is closed, the first core is energized and valve 20 is shifted to the closed position.

A dash-shaped retainer 16 is located in the upper portion of the tank and is provided with apertures 17. A plurality of rods 18 extend downwardly from the collector and pass through the slots 17 in the retainer into a body 14 of slurry located in the tank. The slurry contains coarse solids which are held submerged in the slurry by the retainer 16 as shown in FIG. 4.

Solenoid valve 20 remains in the closed or open condition until one of the cores is energized to change its condition. The cores which control the opening and closing of the valve 20 are energized to perform their respective functions by the momentary closing of switches S1 and S2.

Referring now to FIGS. 1 and 2, it can be seen that the gas collector 12 is free to rotate (as well as slide vertically) in the interior of the tank 11 and that the apertures 17 in the retainer 16 are concentric slots. The tank 11 is provided with a sidewall 19 in the form of a circular tube whose inner surface is a circular cylinder. The collector 12 has an outer surface 21 that slides smoothly in the circular cylindrical surface of the tank. The retainer 16 rests on an annular ledge 22 which is fixed to the inner surface of the tank. The retainer is like a sewer cover and has sufficient weight, so that it is not easily moved from its position of rest on the ledge 22 by the coarse material beneath it.

An overflow pipe 23 is located on the tank a substantial distance above the retainer 16 to regulate the slurry level 11 between the tank and jacket 33 to maintain the slurry at a predetermined temperature for digestion of slurry and solids.

The feed means 13 that is provided for introducing raw coarse organic feed material into the tank consists of a feed tube 25 extending vertically downwardly from the top wall of the gas collector. The tube has a conical entrance portion 26 and the slurry or solid organic matter is introduced under pressure by a concentric feed screw 27. The feed tube 25 extends through a central circular aperture 28 formed in the retainer 16.

The operation of the invention will now be readily understood in view of the above discussion. The raw stock is introduced into the apparatus by the rotation of the feed screw 27 in the tube 25 with its conical entrance 26. Raw organic matter or stock may be in the form of animal manure, industrial, agricultural, and domestic waste, garbage, and even normal trash which has been nominally masticated or chopped. Water or liquid waste is added directly to the generator or added to the stock to give a thick slurry which is introduced into the generator. When the feed rate is regulated properly, a certain amount of spent slurry will pass outwardly through the overflow pipe 23 in direct proportion to the amount introduced. As methane gas is generated in the body 14 of slurry, the gas flows upwardly through the portions of the slots 17 in the retainer 16 that are not occupied by the rods 18 and accumulates in the collector 12. Eventually, this will cause the collector to move upwardly so that a finger 34 at the top of the collector 12 closes upper level switch S1 which causes the solenoid valve 20 to open and release the accumulated methane gas through the conduit 15 to a storage container or for immediate use as fuel in burning and like processes in home, farm or business. Any excess can, of course, be sold. Some of the gas necessarily must be used in producing the hot water for heater 30 used for heating the generator with the heat-exchanger 24.

As the gas is released from the collector 12, the collector moves downwardly until finger 34 closes lower level switch S2 which energizes the first core and causes the solenoid valve 20 to close. Solenoid valve 20 remains in the closed condition until the collector 12 again rises to the level where switch S1 closes to shift the solenoid valve 20 to the open condition.

The collector 12 moves up and down as gas that is generated in the generator is accumulated in the collector and released from the collector. This causes the rods 18 to move up and down through the slots 17 and serve to open up the coarse solids submerged in the slurry, so that the suspended solids cannot form a hard mat on the upper surface of the slurry and prevent the release of gas. In addition to providing the vertical motion of the rods 18, the collector is capable of rotating to and fro and, since the conduit 15 is flexible, this rotation causes the rods to further break up the solids submerged in the body 14 of slurry and held down by the retainer. The retainer holds down the solids immersed within the slurry and thereby facilitates the process of bioconversion.

Figure 3:
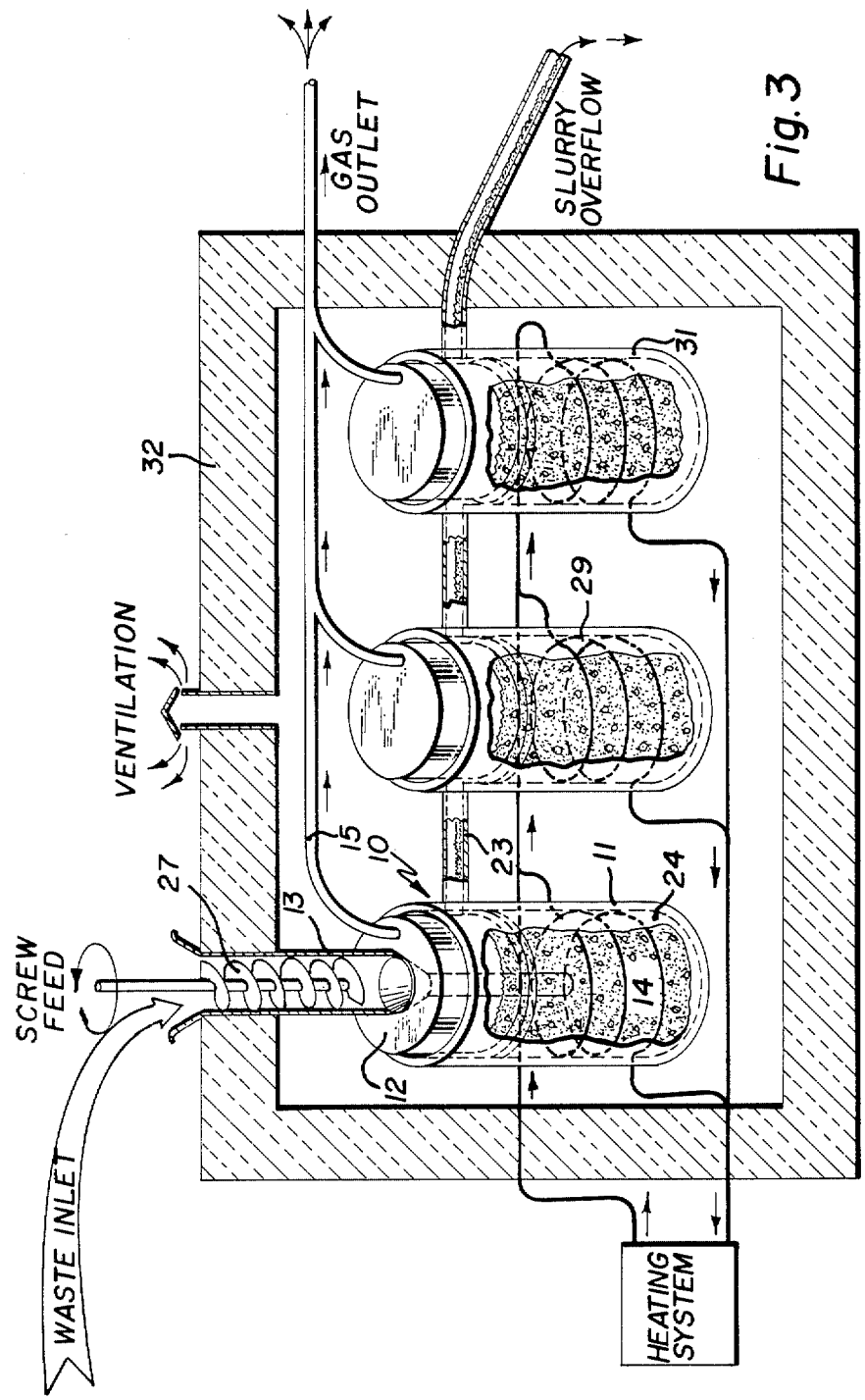
FIG. 3 is a vertical sectional view of a unit making use of a plurality of the generators.

FIG. 3 shows an arrangement in which three methane generators 11, 29, and 31 are enclosed in an insulated housing 32 and used to carry on the operation. In this case, the rate of feed of slurry brought about by the screw 27 is selected in an amount such that complete conversion to methane does not take place in only one generator, so that it is necessary to use a battery of generators. This results in an increase of generator capacity by adding generators as required. The rate of feed and operation is selected such that the spent effluent can be dried or directly used as fertilizer. Properly operated, the spent slurry is odorless or has a mild marshy odor. Based on the performance of a 20 gallon methane generator constructed in accordance with the basic principles of the present invention, it is possible to evaluate the feasibility of a small methane generator on a farm having one or two cows. The basic generator is generally similar to the construction shown in FIG. 3 and consists of three 300-gallon fiberglass tanks, each of which were 36 inches in diameter and 7 feet tall. They are provided with 30-inch high floating gas collectors and nearly 3600 cubic feet of the gas was stored in inflatable vinyl bags protected by fencing. Normally, 120 lbs. of manure are diluted with 40 lbs. of water to 160 lbs. (that is to say, 12% solids) and the thick slurry is fed into the generator. The generator tanks are interconnected and the spent slurry left the third tank after nearly 45 days of retention time. This arrangement will produce 120 cubic feet of biogas per day. The loading rate could increase to almost 320 lbs. per day with 20 days retention time to obtain 240 cubic feet of gas daily. The three tanks are clustered together, wrapped with 180 feet of ½ inch diameter soft copper tubing, and provided with a heavily insulated enclosure. Hot water is circulated through the copper tubing to maintain 104° F. (40° C.) throughout the year. It can be seen that the entire system is passive and requires little attention or repair.

For proper operation of the unit, one must assume the following conditions:

1. The installation is on a farm or a municipal waste dump area where there are no legal or social restrictions.
2. All possible effort is made to minimize heat loss from the generators, so that it does not take more than 10% of the gas produced per day to maintain the 104° F. temperature.
3. The labor for the installation of the tank and the fabrication and installation of the gas collectors and the necessary alterations to accommodate the system are provided by the owner without charge. It is felt, therefore, that, if it is necessary to provide professional installation, spent slurry in the amount of about 2 tons can be sold as fertilizer for about $75/ton in exchange for such labor.
4. The evaluation assumes that fuel costs continue to rise at about 10% per year.
5. Alternative energy is available for peak demands.
6. The services of a competent and enthusiastic consultant are available.

It should be kept in mind that the coarse material is retained under the retainer 16. The advantage of this is that it (a) need not be commuted to make a fine slurry, and (b) it is retained at the favorable micro-organism level or environment. It is *always* submerged in the active environment (bathed from all sides by liquid).

The solids that are fed through the screw feed 27 into the depth of slurry in tank 11 float up but kept submerged in the slurry under the retainer 16. These are acted upon by microbes and gas is released. The vertical and rotative action of the floating gas collector 12 and its rods give *free* mechanical action to keep the dense mass open for gas to escape. That is to say, no external energy need be provided for: (a) reducing the bulky solids into fine particles to be made into slurry, (b) keeping the particles in suspension by thorough and continuous agitation in the generator tank during microbiological bioconversion action on them, and (c) piercing open the mat that forms under the retainer in the slurry. All of these functions are accomplished by harnessing the mechanical advantages of natural forces of buoyancy, gas pressure, relative densities, gravitational flow, etc.

The leakage of finer solids upwardly through slots and apertures in the retainer are small and immaterial.

The material costs come to about $2,000 and, when this money is obtained in the form of a loan, the savings will pay off this loan in around 6 years. After the loan is repaid, the generator will continue to produce gas valued at no less than $550 per year. In addition, such a methane generator operating on a small farm will go far in reestablishing the symbiosis between the human being and the environment by making use of the "waste" to provide energy and fertilizer through a natural process of recycling.

It is obvious that minor changes may be made in the form, construction and applications of the invention without departing from the material spirit thereof. It is not, however, desired to confine the invention to the exact form herein shown and described, but it is desired to include all such as properly come within the scope claimed.

The invention having been thus described, what is claimed as new and desired to secure by Letters Patent is:

1. Methane generator, comprising:
   (a) a tank having an open top,
   (b) a gas collector vertically slidable in the tank,
   (c) feed means for introducing a slurry of liquid and raw solid organic material through the gas collector into the tank,
   (d) conduit means for removing methane from the collector,
   (e) a retainer located in the upper portion of the tank and extending horizontally across substantially the entire cross-section of the tank to maintain the solid organic material submerged in the slurry, the retainer having apertures, and
   (f) rods extending downwardly from the collector and passing through the apertures in the retainer into the solids floating in the slurry beneath the retainer, wherein the gas collector is free to rotate in the tank, and wherein the apertures in the retainer are concentric slots.

2. Methane generator as recited in claim 1, wherein the tank is provided with a side wall in the form of a circular tube whose inner surface is a circular cylinder, and wherein the gas collector has an outer surface that slides smoothly in the circular cylindrical surface of the tank.

3. Methane generator as recited in claim 2, wherein the retainer rests on an annular ledge fixed to the inner surface of the tank and has sufficient weight that it is not easily lifted or moved from its position on the ledge.

4. Methane generator as recited in claim 3, wherein an overflow pipe is located on the tank a substantial distance above the retainer.

5. Methane generator as recited in claim 1, wherein a heat exchanger is wrapped around the lower portion of the tank to maintain the material at a predetermined temperature for optimum methanogenic microbial action.

6. Methane generator as recited in claim 5, wherein the means for introducing raw feed material consists of a feed tube extending vertically downwardly from a horizontal top wall of the gas collector, the tube having a conical entrance portion, and wherein the material is introduced under pressure provided by a helical feed screw.

7. Methane generator as recited in claim 6, wherein the feed tube extends through a central circular aperture formed in the retainer.

8. Methane generator as recited in claim 7, wherein the tank and collector combination is the first in a series of tank-and-collector combinations, the material passing from the overflow pipe of a preceeding combination to the tank of a following combination.

9. Methane generator as recited in claim 1, comprising:
   (a) a valve located in said conduit, and
   (b) control means for selectively opening and closing the valve so that closure of the valve when the collector is in a predetermined lower position allows gas to accumulate in the collector and causes the collector to rise in the tank to a predetermined upper position and opening of the valve in said upper position allows the gas to escape through the conduit to allow the gas collector to fall to said predetermined lower position.

10. Methane generator as recited in claim 9, wherein said valve is an electrically operated solenoid valve and said control means comprise limit switch means operatively connected to the solenoid valve for automatically opening the solenoid valve at said predetermined upper position and for closing the solenoid valve at said predetermined lower position.

* * * * *